US008883133B2

(12) United States Patent
Leroux et al.

(10) Patent No.: US 8,883,133 B2
(45) Date of Patent: Nov. 11, 2014

(54) PHARMACEUTICAL COMPOSITIONS COMPRISING POLYMERIC BINDERS WITH NON-HYDROLYSABLE THEIR USE IN TREATING CELIAC DISEASE

(75) Inventors: Jean-Christophe Leroux, Montreal (CA); Mohamad Nasser Eddine, Laval (CA)

(73) Assignee: Valorisation-Recherche Limited Partnership, Montreal, Quebec (CA)

( * ) Notice: Subject to any disclaimer, the term of this patent is extended or adjusted under 35 U.S.C. 154(b) by 949 days.

(21) Appl. No.: 12/093,423

(22) PCT Filed: Oct. 27, 2006

(86) PCT No.: PCT/CA2006/001784
§ 371 (c)(1),
(2), (4) Date: May 12, 2008

(87) PCT Pub. No.: WO2007/053935
PCT Pub. Date: May 18, 2007

(65) Prior Publication Data
US 2008/0254099 A1 Oct. 16, 2008

Related U.S. Application Data

(60) Provisional application No. 60/735,820, filed on Nov. 14, 2005.

(51) Int. Cl.
A61K 31/74 (2006.01)
A61K 47/00 (2006.01)
A23L 1/308 (2006.01)

(52) U.S. Cl.
CPC ............... *A61K 31/74* (2013.01); *A23L 1/3084* (2013.01)
USPC ...................... 424/78.18; 424/439; 424/78.01

(58) Field of Classification Search
None
See application file for complete search history.

(56) References Cited

U.S. PATENT DOCUMENTS

| 3,567,461 | A | * | 3/1971 | Wernecke ...................... 426/555 |
| 4,432,967 | A | | 2/1984 | Szymanski |
| 5,527,524 | A | * | 6/1996 | Tomalia et al. .............. 424/1.33 |
| 5,529,884 | A | | 6/1996 | Tutt et al. |
| 5,846,517 | A | * | 12/1998 | Unger .......................... 424/9.52 |
| 6,306,419 | B1 | | 10/2001 | Vachon et al. |
| 6,537,538 | B2 | | 3/2003 | Zaneveld et al. |
| 2002/0028201 | A1 | * | 3/2002 | Bucha et al. .............. 424/140.1 |
| 2002/0114776 | A1 | | 8/2002 | Zaneveld et al. |
| 2002/0128346 | A1 | | 9/2002 | Domschke et al. |
| 2004/0037809 | A1 | | 2/2004 | Quay et al. |
| 2006/0052559 | A1 | | 3/2006 | Gomez et al. |

FOREIGN PATENT DOCUMENTS

| AU | 2006312953 | 11/2011 |
| AU | 2006312953 | 2/2012 |
| AU | 2012202739 | 2/2013 |
| CA | 2561800 | 10/2005 |
| CN | 200680050656 | 4/2012 |
| CN | 201210260973 | 2/2013 |
| CN | 200680050656 | 6/2013 |
| CN | 201210260973 | 9/2013 |
| EP | 06790907 | 11/2013 |
| IL | IS191058 | 10/2009 |
| IL | IS 191058 | 1/2010 |
| IL | IS 191058 | 6/2010 |
| IL | IS 191058 | 4/2011 |
| IL | 212479 | 5/2011 |
| IL | 191058 | 9/2011 |
| IL | 191028 | 3/2013 |
| IL | 212479 | 3/2013 |
| JP | S59-031714 | 1/1984 |
| JP | 2004-525095 | 8/2004 |
| JP | 2008-539200 | 6/2012 |
| JP | 2008-539200 | 3/2013 |
| JP | 2012-122848 | 11/2013 |
| WO | WO 00/28920 A1 | 5/2000 |
| WO | WO-01-49824 | 7/2001 |
| WO | WO-02-49557 | 6/2002 |
| WO | WO-2004-009100 | 1/2004 |
| WO | WO 2004/050714 | 6/2004 |
| WO | PCT/CA2006/001784 | 5/2005 |
| WO | PCT/CA2006/001784 | 2/2007 |
| WO | WO 2007/053935 | 5/2007 |

OTHER PUBLICATIONS

Lukas, J., et al., "Biological properties of . . . ", 2001, Journal of Material Science Material Science in Medicine, 12, pp. 639-646.*
Montgomery, A.M.P. "Low gluten diet in the treatment of adult coeliac disease: effect on jejunal morphology and serum anti-gluten antibodies", 1988, Gut, 29, pp. 1564-1568.*
Collar, C., et al., "Lipid Binding of Fresh and Stored Formulated Wheat Breads. Relationship with Dough and Bread Technological Performance", 2001, Food Science and Technology International, 7(6), pp. 501-510.*
Heylin, M., et al., "Chemistry grads post gains in 2006", 2004, Chemical and Engineering News, pp. 43-52.*
Auricchio, et al. , Mannan and Oligomers of N-Acetylglucosamine Protect Intestinal Mucosa of Celiac Patients . . . , Gastroenterology (1990) vol. 99: 973-978.

(Continued)

*Primary Examiner* — Michael G Hartley
*Assistant Examiner* — Lance Rider
(74) *Attorney, Agent, or Firm* — Finnegan, Henderson, Farabow, Garrett & Dunner LLP.

(57) ABSTRACT

A pharmaceutical composition comprising a polymeric binder including a high molecular weight synthetic polymer having a backbone constituted of non hydrolysable covalent bonds, said polymer being able to form electrostatic bonds at a pH lower than the isoelectric point of gluten and peptides derived from the degradation of gluten, and being able to bind to gluten or peptides derived from the degradation of gluten in the gastrointestinal tract, and a pharmaceutically acceptable carrier. Methods of using the polymeric binder for binding gluten or a peptide derived from the degradation of gluten, for decreasing the degradation of gluten into toxic peptides or for decreasing interaction of gluten or peptides derived from the degradation of gluten with the gastrointestinal mucosa.

19 Claims, 9 Drawing Sheets

(56) References Cited

OTHER PUBLICATIONS

Bolte et al., "Peptic-tryptic digests of gliadin: contaminating trypsin but not pepsin interferes with gastrointestinal protein . . .", Clin Chim Acta (1996), vol. 247: 59-70.

Blanch et al., "New Insight into the Solution Structures of Wheat Gluten Proteins from Raman Optical Activity", Biochemistry, (2003), vol. 42: 5665-5673.

Ciacci et al., "Long-Term Follow-Up of Celiac Adults on Gluten-Free Diet: Prevalence and Correlates of Intestinal Damage" Digestion (2002), vol. 66:178-185.

Christiansen et al., "Papillomavirus microbicidal activities of high-molecular-weight cellulose sulfate . . . ", Antimicro. Agents and Chem. (2001), vol. 45(12): 3427-3432.

Ciccocioppo et al. "The immune recognition of gluten in coeliac disease", Clin. Exp. Immunol., (2005), vol. 140: 408-416.

Drago et al., "Recent developments in the pathogenesis, diagnosis and treatment of celiac disease", Experts Opin. Ther. Patents, (2002), vol. 12(1): 45-51.

Fasano et al., "Zonulin, a newly discovered modulator of intestinal permeability, and its expression in coeliac disease", The Lancet (2000), vol. 355:1518-1519.

Godon et al., "A small scale device for wheat gluten separation", Qual. Plant Foods Hum. Nutr (1983) vol. 33: 161-168.

Guandalini et al., "Update on immunologic basis of celiac disease", Current Opinion in Gastroenterology, (2001), vol. 17: 545-550.

Halsted, Charles H. MD, "The Many Faces of Celiac Disease", New England Journal of Medicine, (1996), vol. 334: 1190-1191, No. 18.

Hausch et al., "Intestinal digestive resistance of immunodominant gliadin peptides", Am. J Physiol Gastrointest Liver Physiol, (2002), vol. 283: G996-G1003.

Kim et al., "Structural basis for HLA-DQ2-mediated presentation of gluten epitopes in celiac disease", PNAS (2004) vol. 101, No. 12: 4175-4179.

Kurtz et al. "GT160-246, a Toxin Binding Polymer for Treatment of Clostridium difficile Colitis", Antimicrob. Agents Chemother. (2001) vol. 45: 2340-2347.

Lukas et al., "Biological properties of copolymer of 2-hydroxyethyl methacrylate . . . ", Journal of Materials Sciences: Materials in Medicine, (2001) vol. 12: 639-646.

Modern Pharmaceutics, 4th edition. Banker GS and Rhodes CT (eds) Marcel Dekker, NY, 2002.

Molberg et al., Mapping of Gluten T-Cell Epitopes in the Bread Wheat Ancestors: Implications for Celiac Disease, Gastroenterology, (2005), vol. 128: 393-401.

Mothes et al., "How gluten-free is gluten-free, and what does this mean to coeliac patients?", Eur. J. Gastroenterol. Hepatol. (2003), vol. 15, 461-463.

Popineau Y., "Fractionation of Acetic Acid-soluble Proteins from Wheat Gluten by Hydrophobic Interaction . . . ", J Cereal Sci, (1985), vol. 3:29-38.

Popineau et al., "Surface Hydrophobicity of Gliadin Components", Cereal Chemistry (1982), vol. 59 (1): 55-62.

Popineau et al., "Fractionation of Gliadins from Common Wheat by Cation Exchange FPLC", J Cereal Sci, (1991), vol. 14: 231-241.

Popineau et al., "Hydrophobic properties of the gliadins of some varieties of Triticum vulgare wheats", Ann Technol. Agric. (1980), vol. 29 (2): 191-204.

Popineau et al., "Fractionation of Wheat Gliadins by Ion-Exchange Chromatography on SP Trisacryl M", Lebensm-Wiss.u.Technol. (1985), vol. 18: 133-135.

Secundo et al., "ATR-FT/IR Study on the Interactions between Gliadins and Dextrin and Their Effects . . . ", J. Agric. Food Chem. (2005), vol. 53: 1757-1764.

Senger et al., "Intranasal administration of a recombinant x-gliadin down-regulates the immune response . . . ", Immunol. Lett. (2003), vol. 88, 2: 127-134.

Shan et al., "Structural Basis for Gluten Intolerance in Celiac Sprue", Science (2002), vol. 297: 2275-2279.

Shan et al., "Intestinal digestive resistance of immunodominant gliadin peptides", Am. J. Physiol. Gastrointest. Liver Phyiol. (2002) vol. 283: G996-G1003.

Shelley et al., "Treatment of dermatitis herpetiformis with cholestyramine", British Journal of Dermatology, (1980), vol. 103: 663-666.

Silano et al., "In vitro screening of food peptides toxic for coeliac and other gluten-sensitive patients: a review", Toxicology, (1999) vol. 132: 99-110.

Sollid L.M., "Coeliac Disease: Dissecting a Complex Inflammatory Disorder", (2002) Nat Rev Immunol , (2002) vol. 2: 647-655.

Sollid et al., "Future Therapeutic Options for Celiac Disease", Nat Clin Pract Gastroenterol Hepatol. (2005) vol. 2 (3), 140-147.

Stenzel-Rosenbaum et al., "Synthesis of Poly(styrene) Star Polymers Grown from Sucrose, Glucose, . . . ", Macromolecules, (2001) vol. 34: 5433-5438.

Trier JS. "Celiac sprue", N England J Med, (1991), vol. 325: 1709-1719.

Vader et al., "Characterization of Cereal Toxicity for Celiac Disease Patients Based on Protein homology in Grains", Gastroenterology, (2003) vol. 125: 1105-1113.

Christensen N. D. et al., Papillomavirus Microbial Activities of High-Molecular-Weight Cellulose Sulfate, Dextran Sulfate, and Polystyrene Sulfonate:, Antimicrobial Medicine 2001, vol. 45, No. 12, pp. 3427-3432.

Lukas J. et al., "Biological Properties of Copolymer of 2-Hydroxyethyl Methacrylate with Sulfopropyl Methacrylate", Journal of Materials Sciences: Materials in Medicine 2001, vol. 12, pp. 639-646.

Liang et al., "Interaction of a-Gliadin With Polyanions: Design Considerations for Sequestrants Used in Supportive Treatment of Celiac Disease", Biopolymers, 93(5): 418-428, May 2010.

Liang et al., "Interaction of a-Gliadin With Poly(HEMA-Co-SS): Structural Characterization and Biological Implication", Biopolymers, 91(2): 169-178, 2009.

Pinier et al.; "Polymeric Binders Suppress Gliadin-Induced Toxicity in the Intestinal Epithelium", Gastroenterology (2009); pp. 288-298.

IUPAC, "A Brief Guide to Polymer Nomenclature", 2012, accessed from: htt/:/www.iupac.org/publications/ci/2012/3406/Brief-Guide-to-Polymer-Nomenclature-v1.1p_121102.pdf, pp. 1-2.

Office Action issued Oct. 30, 2012, Japanese App. No. 2008-539200.

Office Action issued Dec. 4, 2012, Canadian App. No. 2,629,327.

Office Action issued Dec. 6, 2012, Mexican App. No. 08/06233.

Office Action issued Feb. 24, 2010 in China patent App. No. 200680050656.8.

Office Action issued in Russia App. No. 2008123835/15(028878) due Jan. 10, 2010.

U.S. Appl. No. 13/461,468, Office Action, filed Feb. 14, 2013, Leroux.

* cited by examiner

PHARMACEUTICAL COMPOSITIONS COMPRISING POLYMERIC BINDERS WITH NON-HYDROLYSABLE THEIR USE IN TREATING CELIAC DISEASE

CROSS-REFERENCE TO RELATED APPLICATIONS

This application is a National Entry Application of PCT application no PCT/CA2006/001784 filed on Oct. 27, 2006 and published in English under PCT Article 21(2), which itself claims priority on U.S. provisional application Ser. No. 60/735,820, filed on Nov. 14, 2005. All documents above are incorporated herein in their entirety by reference.

FIELD OF THE INVENTION

The present invention relates to pharmaceutical compositions comprising polymeric binders, and methods of use thereof. More specifically, the present invention is concerned with non-digestible synthetic polymers for binding gluten or gliadin and/or -peptides derived from the degradation of gluten or gliadin and methods of use thereof.

BACKGROUND OF THE INVENTION

Celiac disease, also known as gluten intolerance is a syndrome characterized by damage to the small intestinal mucosa, following exposure to either the gliadin fraction of wheat gluten or similar alcohol soluble proteins (prolamines) of barley and rye in genetically susceptible subjects. Celiac disease is a common autoimmune disorder that has genetic, environmental and immunologic components. The disease is closely associated with genes that code for human leukocyte antigens DQ2 and DQ8 (1). A 33-mer fragment of α-gliadin was identified that has several characteristics suggesting it is a possible initiator of the inflammatory response to gluten in celiac disease patients (2).

Symptoms of celiac disease can range from mild weakness, bone pain, and aphthous stomatitis to chronic diarrhea, abdominal bloating, and progressive weight loss (3). Because of the broad range of symptoms, celiac disease presence can be difficult to diagnose. Those affected suffer damage to the villi (shortening and villous flattening) in the lamina propria and crypt regions of their intestine (3). Furthermore, gastrointestinal carcinoma or lymphoma develops in up to 15 percent of patients with untreated or refractory celiac disease (4). A gluten-free diet can prevent almost all complications of the disease (5). Such a diet involves avoiding all products that contain wheat, rye, barley, or any of their derivatives. This is a difficult task as many hidden sources of gluten can be found in the ingredients of many processed foods.

Until now, aside from excluding gluten-containing foods from their diet, no pharmacological treatment is available for celiac patients. Surprisingly, relatively few treatment strategies are currently being explored. Approaches based on the tolerance of antibody and T-cell mediated response to the gliadin toxic peptides or on the development of anti-IL-15 neutralizing antibodies blocking the IL-15 mediated changes in the small intestinal mucosa are under investigation (6). A promising avenue lies in the discovery of exogenous enzymes, which could rapidly degrade toxic peptides in situ (7). However, the high cost associated to large-scale enzyme production and possible loss of activity after oral administration are potential constraints to their commercialization. Complementary strategies aiming to interfere with activation of gluten-reactive T cells include the inhibition of binding of gluten peptides to human leukocyte antigen (HLA) DQ2 (or DQ8). The crucial role of HLA in celiac disease development makes it an obvious target for therapeutic intervention. The recently solved X-ray crystal structure of HLA-DQ2 complexed with a deaminated gluten peptide has provided important information for the development of an HLA-DQ2-blocking compound (8). Zonulin antagonists have also been suggested as therapy for celiac disease. Zonulin is a protein involved in the regulation of intercellular tight junctions in the small intestine. Its expression has been shown to increase during the acute phase of celiac disease, a clinical condition in which the intestinal permeability is increased (9).

The development of grains that have low or no content of immunotoxic sequences, but with reasonable baking quality, has also been investigated. Such grains can potentially be developed by selective breeding of ancient wheat varieties (10), by transgenic technology involving mutation of sequences giving rise to immunostimulatory sequences (11) or by incorporation of nontoxic gluten genes into harmless organisms such as rice (12). Although these grains are technically challenging to engineer, and there is a possibility that cross-pollination with gluten-containing grains might lead to reintroduction of immunotoxic sequences, the availability of such grains could give patients with celiac disease a nutritionally better diet.

Polymeric Binders

A number of polymeric binders have been used for treating or preventing certain diseases.

The classic example of a polymeric binder is cholestyramine, a cationic resin that sequesters biliary acids in the gut and consequently lowers cholesterol blood levels. Recently, sevelamer hydrochloride, a novel aluminum and calcium-free polymeric phosphate binder with negligible side effects has been commercialized for the treatment of hyperphosphatemia in patients on dialysis. Perhaps the most interesting discovery in this field is an anionic high-molecular weight polymer, GT160-246, which was shown to neutralize *Clostridium difficile* toxin A activity both in vitro and in vivo (13). This endotoxin is the most commonly identified cause of infectious nosocomial diarrhea. GT160-246 offers a promising and safe nonantimicrobial approach to the treatment and prevention of *C. difficile* colitis in humans.

The idea that high molecular weight polymers could be of potential use in celiac disease stemmed from a study of Auricchio et al. (14), which demonstrated that mannan (mannose homopolysaccharide) and acetylglucosamine oligomers exhibited a protective effect on intestinal mucosa specimens of patients with active celiac disease (14). These findings suggest that the agglutinating and toxic peptides are bound by these carbohydrates. Secundo et al. (26) explored the effect of an other polysaccharide, dextrin on the secondary structure of gliadins and hypothesized that dextrin might be used to prepare non toxic food derivatives for patients suffering from celiac disease. Despite these interesting preliminary data, no further investigations were carried out to confirm those findings in vivo. The main drawback of natural carbohydrates is their degradability under in vivo conditions which would make them inactive in situ.

The present invention seeks to meet these needs and other needs.

The present description refers to a number of documents, the content of which is herein incorporated by reference in their entirety.

SUMMARY OF THE INVENTION

More specifically, in accordance with an aspect of the present invention, there is provided a pharmaceutical composition comprising a polymeric binder including a high molecular weight synthetic polymer having a backbone constituted of non hydrolysable covalent bonds, said polymer being able to form electrostatic bonds at a pH lower than the isoelectric point of gluten and peptides derived from the degradation of gluten, and being able to bind to gluten or peptides derived from the degradation of gluten in the gastrointestinal tract, and a pharmaceutically acceptable carrier.

In a specific embodiment of the pharmaceutical composition, the polymeric binder is able to form hydrophobic interactions with gluten or peptides derived from the degradation of gluten. In an other specific embodiment of the pharmaceutical composition, the polymeric binder is able to form hydrogen bonds. In an other specific embodiment of the pharmaceutical composition, the polymeric binder is able to specifically bind to gluten or peptides derived from the degradation of gluten in the gastrointestinal tract. In an other specific embodiment of the pharmaceutical composition, the polymeric binder is able to bind to gluten or peptides derived from the degradation of gluten in the intestinal tract. In an other specific embodiment of the pharmaceutical composition, the polymeric binder is a copolymer of hydroxyethyl methacrylate (HEMA) and 4-styrene sulfonic acid sodium salt hydrate (SStNa). In an other specific embodiment of the pharmaceutical composition, the polymeric binder is a polymer of 4-styrene sulfonic acid sodium salt hydrate (SStNa). In an other specific embodiment of the pharmaceutical composition, the polymeric binder is a polymer of sulfopropyl methacrylate potassium salt (SPMAK).

In an other specific embodiment of the pharmaceutical composition, the polymeric binder is linear. In an other specific embodiment of the pharmaceutical composition, the polymeric binder is star-shaped. In an other specific embodiment of the pharmaceutical composition, the polymeric binder is a 3 to 18-arm star-shaped copolymer. In an other specific embodiment of the pharmaceutical composition, the polymeric binder is a 5 to 18-arm star-shaped copolymer. In an other specific embodiment of the pharmaceutical composition, the polymeric binder is a 5-arm star-shaped copolymer. In an other specific embodiment of the pharmaceutical composition, the polymeric binder is a 8-arm star-shaped copolymer. In an other specific embodiment of the pharmaceutical composition, the polymeric binder is a 18-arm star-shaped copolymer. In an other specific embodiment of the pharmaceutical composition, the polymeric binder is a copolymer of HEMA and SStNa and has a HEMA/SStNa molar percentage ratio between about 93.5/6.5 and about 1/99. In an other specific embodiment of the pharmaceutical composition, the copolymer is linear HEMA/SStNa (51.5/48.5 mol %). In an other specific embodiment of the pharmaceutical composition, the copolymer is linear HEMA/SStNa (43/57 mol %). In an other specific embodiment of the pharmaceutical composition, the copolymer has a HEMA/SPMAK molar percentage ratio between about 93.5/6.5 and about 1/99.%). In an other specific embodiment of the pharmaceutical composition, the copolymer has a HEMA/SPMAK molar percentage ratio between about 86/14 and about 1/99.

In an other specific embodiment of the pharmaceutical composition, the copolymer is linear HEMA/SPMAK (45/55 mol %).

In an other specific embodiment, the pharmaceutical composition of the present invention further comprises a zonulin antagonist or an HLA DQ2 inhibitor.

In accordance with an other aspect of the present invention, there is provided a method of using the polymeric binder of the present invention comprising administering to a patient suffering from celiac disease a pharmaceutically effective amount of said polymeric binder.

In a specific embodiment, the method of the present invention is for binding gluten or a peptide derived from the degradation of gluten in the patient.

In an other specific embodiment, the method of the present invention is for decreasing the degradation of gluten into toxic peptides in the patient.

In an other specific embodiment, the method of the present invention is for decreasing interaction of gluten or peptides derived from the degradation of gluten with the gastrointestinal mucosa of the patient.

In an other specific embodiment of the method of the present invention, said administration is performed before or during a gluten-containing meal of said patient. In an other specific embodiment of the method of the present invention, said administration is performed after a gluten-containing meal of said patient.

In accordance with an other aspect of the present invention, there is provided a use of the polymeric binder of the present invention in the preparation of a medicament.

In accordance with an other aspect of the present invention, there is provided a use of the polymeric binder of the present invention for binding gluten or a peptide derived from the degradation of gluten in the gastrointestinal tract of a patient in need thereof.

In accordance with an other aspect of the present invention, there is provided a use of the polymeric binder of the present invention in the preparation of a medicament for binding gluten or a peptide derived from the degradation of gluten in the gastrointestinal tract of a patient in need thereof.

In accordance with an other aspect of the present invention, there is provided a use of the polymeric binder of the present invention for decreasing interaction of gluten or peptides derived from the degradation of gluten with the gastrointestinal mucosa of a patient in need thereof.

In accordance with an other aspect of the present invention, there is provided a use of the polymeric binder of the present invention in the preparation of a medicament for decreasing interaction of gluten or peptides derived from the degradation of gluten with the gastrointestinal mucosa of a patient in need thereof.

In accordance with an other aspect of the present invention, there is provided a use of the polymeric binder of the present invention for decreasing degradation of gluten into toxic peptides in the gastrointestinal tract of a patient in need thereof.

In accordance with an other aspect of the present invention, there is provided a use of the polymeric binder of the present invention in the preparation of a medicament for decreasing the degradation of gluten into toxic peptides in the gastrointestinal tract of a patient in need thereof.

In a specific embodiment of the use of the present invention, the patient suffers from celiac disease.

In accordance with yet an other aspect of the present invention, there is provided food comprising the polymeric binder of the present invention.

In a specific embodiment of the food of the present invention, said food is a gluten-containing food. In a specific embodiment of the food of the present invention, said food is bread.

In accordance with yet an other aspect of the present invention, there is provided a method of using the food of the present invention, comprising administering said food to a patient suffering from celiac disease during the patient's meal. In a specific embodiment, the method of the present invention is for binding gluten or a peptide derived from the degradation of gluten contained in the meal of the patient. In an other specific embodiment, the method of the present invention is for decreasing the degradation into toxic peptides of gluten contained in the meal of the patient. In a specific embodiment, the method of the present invention is for decreasing interaction of gluten or peptides derived from the degradation of gluten with the gastrointestinal mucosa of the patient.

In accordance with yet an other aspect of the present invention, there is provided a method of making food for a patient suffering from celiac disease, comprising incorporating into said food the polymeric binder of the present invention. In a specific embodiment of the method of the present invention, said food is a gluten-containing food.

The present invention concerns a high molecular weight inert and non-absorbable polymeric binder, which for use to adsorb gluten and/or its degradation products. Such a system will help prevent or decrease gluten's deleterious effects on the gastrointestinal mucosa. Without being so limited, it is hypothesized that peptide binding to the polymer has two effects. First, the enzymatic degradation and generation of toxic fragments is slowed down by gluten and/or by its degradation product's adsorption on an inert support. Second, complexation with a high molecular weight polymer decreases peptide absorption and the subsequent immune response. This system thus provides a prevention adjuvant for patients faced with situations where the absence of gluten residues cannot be ascertained or when gluten free meals are not available.

Although specific non-digestible synthetic polymers are presented herein, the invention is not so limited. As used herein, the terms "non-digestible" when used to qualify the polymers of the present invention, is meant to refer to a polymer having a backbone constituted of non hydrolysable covalent bonds. It is believed that a person of ordinary skill in the art may easily identify other non-digestible synthetic polymers that can be used in accordance with the present invention. Similarly, the polymers specifically described herein can be optimized to maximize their affinity towards gluten and its degradation products and minimize their binding to other proteins. Of course, a certain proportion of these proteins/peptides will escape adsorption onto the polymers of the present invention but it has been suggested that a daily intake of gliadin of 4-14 mg does not cause small-intestinal mucosal damage in celiac patient (15). Such a system would certainly not replace a gluten free diet as main treatment. However, it could be used occasionally as a prevention adjuvant when patients face situations where absence of gluten residues cannot be ascertained or when gluten free meals are not available.

The polymeric binders of the present invention may advantageously reduce the oral absorption of gluten and peptides derived thereof. These polymeric binders act in the gastrointestinal tract without being absorbed into the bloodstream, thereby minimizing the potential for adverse effects caused by the polymer itself. At a pH lower than the isoelectric point of gluten and peptides derived thereof, the polymeric binders are negatively charged while these proteins and peptides are positively charged allowing for the formation of electrostatic interactions. These polymeric binders also may also form hydrophobic interactions with these proteins and peptides. In specific embodiments, the polymeric binders of the present invention also have an ability to form hydrogen bonds. Although this last characteristic may be desirable, it was shown not to be essential since it certain polymers of the present invention, e.g. homopolymer of sulfopropyl methacrylate potassium salt (SPMAK), that do not possess this characteristic were found to be able to bind to gluten. Without being so limited, such polymeric binders can be synthesized with monomers presented in Table 1 below. People of ordinary skill in the art may select combinations of one or more of these (or other) monomers to form polymeric binders of the present invention:

TABLE 1

Styrene derivatives:

Styrene sulfonate.
Styrene sulfate.
Styrene sulfanilate.
Sulfophenyl alanine.
Tyrosine sulfate.
Sulfophenethyl acrylamide.
Sulfophenethyl methacrylamide.
Vinylnaphthalene sulfonate.
Vinylnaphthalene sulfate.
Vinylbiphenyl sulfonate.
Vinylbiphenyl sulfate.
Anethole sulfonate.
Styrenes with crown ether moieties.
Styrenes substituted with N,N-dialkylamido groups.
4-methoxystyrene.
4-(2-(N,N-dimethylamino)ethyl) styrene.
4-(2-(N,N-dimethylamino)methyl) styrene
4-(2-(N,N-diethylamino) ethyl) styrene
4-bis(N,N-diethylamino)phosphino-α-methyl styrene.
4-vinylphenol.
3-vinylcatechol.
4-vinylacetophenone.
4-vinylbenzoic acid.
3-vinylbenzoic acid
2-(4-vinylphenyl)-1,3-dioxolane.
2-(4-vinylphenyl)-1,3-dioxane.
4-dimethoxymethylstyrene-(4-vinylbenzaldehyde dimethylacetal).
2-(2-vinylphenyl)-1,3-dioxolane.
2-(3-vinylphenyl)-1,3-dioxolane.
1-(4-vinylphenyl)-4-methyl-2,6,7-trioxabicyclo[2.2.2]octane.
4-(2-hydroxyethyl) styrene
4-(3-hydroxypropyl) styrene
4-{[4-(4-vinylphenyl)butoxy]methyl}-1-methyl-2,6,7-trioxabicyclo[2.2.2]octane.
4-vinylthiophenol.
4-(2-mercaptoethyl) styrene.
2-(4-vinylphenyl)-2-oxazoline.
N,N-diethyl-4-vinylbenzenesulfonamide.
N-methyl-N-[(4-vinylphenyl)sulfonyl]piperazine.
4-aminostyrene.
3-aminostyrene
4-aminomethylstyrene.
3-aminomethylstyrene.
4-(2-aminoethyl)styrene.

Styrene bearing hydroxyl group(s):

(p-Vinylbenzamido)-β-chitobiose.
(p-vinylbenzamido)-β-lactose.
N-(p-vinylbenzyl)-L-gulonamide.
N-(p-vinylbenzyl)-6-D-glucaramide.
N-(p-vinylbenzyl)-6-D-glucaramid-1-ate.
4-Acrylamidophenyl-β-lactoside.
N-(p-vinylbenzyl)-D-glucoronamide.
4-vinylbenzyl-D-gluco(D-manno)hexitol.
p-[2-[N-(p-vinylbenzyl)carbamoyl]ethyl]phenyl α-D-mannopyranoside.
p-[2-[N-(p-vinylbenzyl)carbamoyl]ethyl]phenyl β-D-mannopyranoside.
N-(p-vinylbenzyl)-5[O-β-D-galactopyranosyl-(1→4)]-D-gluconamide.
α-mannopyranoside.
β-mannopyranoside.

Acrylic monomers:

Glycidyl acrylate.
2-Hydroxyethyl acrylate.
2-Hydroxyethyl methacrylate.
Hydroxypropyl methacrylate.
2-(N,N-Dimethylamino)ethyl methacrylate.
2-(N,N-Diethylamino)ethyl methacylate
3-Sulfopropyl methacrylate.
Tetrahydropyranyl methacrylate.
Benzyl methacrylate.

TABLE 1-continued 2-gluconamidoethyl methacrylate.
2-lactobionamidoethyl methacrylate.
2-(2',3',4',6'-tetra-O-acetyl-β-D-glucopyranosyloxy)ethyl acrylate.
(4,5-dihydroxy-6-hydroxymethyl-3-methylcarboxamidotetrahydro-2H-2-pyranyloxy)ethyl acrylate.
Sulfated monomers:

Vinyl sulfate.
Propene sulfate.
Butene sulfate.
Pentene sulfate.
Hexene sulfate.
Heptene sulfate.
Octene sulfate.
Nonene sulfate.
Decene sulfate.
Undecene sulfate.
Dodecene sulfate.
Sulfonated monomers:

Vinyl sulfonate.
Propene sulfonate.
Butene sulfonate.
Pentene sulfonate.
Hexene sulfonate.
Heptene sulfonate.
Octene sulfonate.
Nonene sulfonate.
Decene sulfonate.
Undecene sulfonate.
Dodecene sulfonate.
Phosphated monomers:

Vinyl phosphate.
Propene phosphate.
Butene phosphate.
Pentene phosphate.
Hexene phosphate.
Heptene phosphate.
Octene phosphate.
Nonene phosphate.
Decene phosphate.
Undecene phosphate.
Dodecene phosphate.
Others:

Maleic anhydride.
N-acryloylated 3'-sulfo-Lewis$^x$-Glc monomer.
α-sialoside acrylamide.
N-vinylpyridine.
N-vinylpyrrolidinone.
Vinyl imidazole.
1,3-Dimethyl-2-(4-vinylphenyl)imidazolidine.
3-(N-acryloylamino)propyl-O-(β-D-galactopyranosyl)-(1→4)-2-acetamido-2-deoxy-β-D-glucopyranoside.
6-(N-acryloylamino)hexyl-O-(β-D-galactopyranosyl)-(1→4)-2-acetamido-2-deoxy-β-D-glucopyranoside.
3-(N-acryloylamino)propyl 2-acetamido-2-deoxy-β-D-glucopyranoside.
6-(N-acryloylamino)hexyl 2-acetamido-2-deoxy-β-D-glucopyranoside.
n-pentenyl β-D-galactopyranoside.
n-pentenyl-O-(2-acetamido-2-deoxy-β-D-glucopyranosyl)-(1→4)-2-acetamido-2-deoxy-β-D-glucopyranoside.
n-pentenyl-O-(β-D-galactopyranosyl)-(1→4)-2-acetamido-2-deoxy-β-D-glucopyranoside.
n-pentenyl-O-(β-D-galactopyranosyl)-(1→4)-β-D-glucopyranoside.
n-pentenyl-O-(β-D-galactopyranosyl)-(1→4)-[O-(α-L-fucopyranosyl)-(1→3)]-2-acetamido-2-deoxy-β-D-glucopyranoside.
n-pentenyl-O-(β-D-galactopyranosyl)-(1→6)-2-acetamido-2-deoxy-β-D-glucopyranoside.
n-pentenyl-O-(β-D-galactopyranosyl)-(1→3)-2-acetamido-2-deoxy-β-D-glucopyranoside.
n-Alkenyl-2-acetamido-2-deoxy-α-D-glucopyranosides (and sulfated derivatives);
2-N-acryloyl-aminoethoxyl 4-O-(β-D-galactopyranosyl)-β-D-glucopyranoside (and sulfated derivatives).
N-maleicamido-2-deoxy-glucose sodium salt.
N-maleicamido-1-deoxy-lactitol sodium salt.
Fucose-7-oxanorbornene derivative.
C-Glc-7-oxanorbornene derivative.
C-Man-7-oxanorbornene derivative.
Unsymmetrical glucose containing 7-oxanorbornene derivative.
O-Glc-7-oxanorbornene derivative.
O-Man-7-oxanorbornene derivative.
Unsymmetrical mannose containing 7-oxanorbornene derivative.
O-Man norbornene derivative.
sugar derivatized poly(7-oxanorbornene)s.
sugar derivatized poly(norbornene)s.

While the polymeric binders of the present invention have backbone constituted of non hydrolysable covalent bonds, they may also comprise side chains containing hydrolysable covalent bonds.

As used herein the term "gluten" refers to a protein group found in various cereals. Gluten can be fractioned into the ethanol-soluble prolamines and ethanol-insoluble glutenins. Alcohol-soluble prolamines from wheat, rye, barley and possibly oats are toxic in celiac patients. A common feature of the wheat prolamine is a high content of glutamine (>30%) and proline (>15%). The wheat prolamines are subdivided into α/β, γ and ω gliadins containing similar or repetitive glutamine and proline-rich peptide epitopes that appear to be responsible for the observed toxicity of gluten.

As used herein, the term "peptide derived from the degradation of gluten" refers to any peptide derived from the degradation of gluten that would desirably bind to the polymers of the present invention after gluten intake. Without being so limited it includes all peptides listed in Ciccocioppo (23).

As used herein, the term "high molecular weight polymer" refers to a polymer having a molecular weight comprised between 5,000 and 5,000,000 g/mol.

As used herein, the term "pharmaceutically acceptable carrier" refers to a solution, suspension, emulsion, tablet or capsule prepared with commonly used excipients such as those described in Modern Pharmaceutics (27).

As used herein, the term "pharmaceutically effective amount" of a polymer of the present invention refers to an amount that is effective for decreasing interaction of gluten or peptides derived from the degradation of gluten with the gastrointestinal mucosa after gluten intake of a patient in need thereof. Without being so limited, the effective amount of the polymer of the present invention may be from about 200 mg up to about 15 g per day (e.g., 200 mg; 250 mg; 300 mg; 500 mg; 750 mg; 1 g; 1.5 g; 2 g; 2.5 g; 3 g, 5 g; 7.5 g).

As used herein, the term "specifically binds" in the expression "polymer binder that specifically binds to gluten or peptides derived from the degradation of gluten" refers to the ability of the polymer to bind more in the gastrointestinal tract to proteins or peptides derived from food intake that are hydrophobic such as gluten and peptides derived thereof than they bind to other food proteins such as casein and/or albumin.

The present invention encompasses linear and star-shaped polymers. Star-shaped polymers according to specific embodiments of the present invention have 3 to 18 arms.

As used herein the term "patient in need thereof" refers to a human affected by celiac disease that is eating or has eaten a gluten-containing meal.

The articles "a," "an" and "the" are used herein to refer to one or to more than one (i.e., to at least one) of the grammatical object of the article.

The term "including" and "comprising" are used herein to mean, and re used interchangeably with, the phrases "including but not limited to" and "comprising but not limited to".

The term "such as" is used herein to mean, and is used interchangeably with, the phrase "such as but not limited to".

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Materials

α-Gliadin was kindly supplied by the Institut National de la Recherche Agronomique, (Nantes, France). It was purified from soft wheat as described by Popineau et al. (16-21). Briefly, after extraction of crude gliadin from gluten (isolated from flour), gliadin subgroups were separated and purified successively by ion exchange chromatography, size exclusion chromatography and finally hydrophobic interaction chromatography.

Bovine albumin was purchased from Serological Proteins (Kankakee, Ill.). α-Casein (from bovine milk), SStNa, HEMA, SPMAK, R-D-glucose, α-cyclodextrin hydrate, sucrose (98%), poly(ethylene glycol) (PEG) ($M_n$ 2000), 2-bromoisobutyryl bromide, copper bromide Cu(I)Br and 2,2'dipyridyl were all purchased from Sigma-Aldrich (St Louis, Mo.) and used as received. Eppendorff tubes, pipette tips and 96-well plates (Maximum Recovery) were provided from Axygen Scientific (Union City, Calif.).

Synthesis of the Initiators

Figure 1:
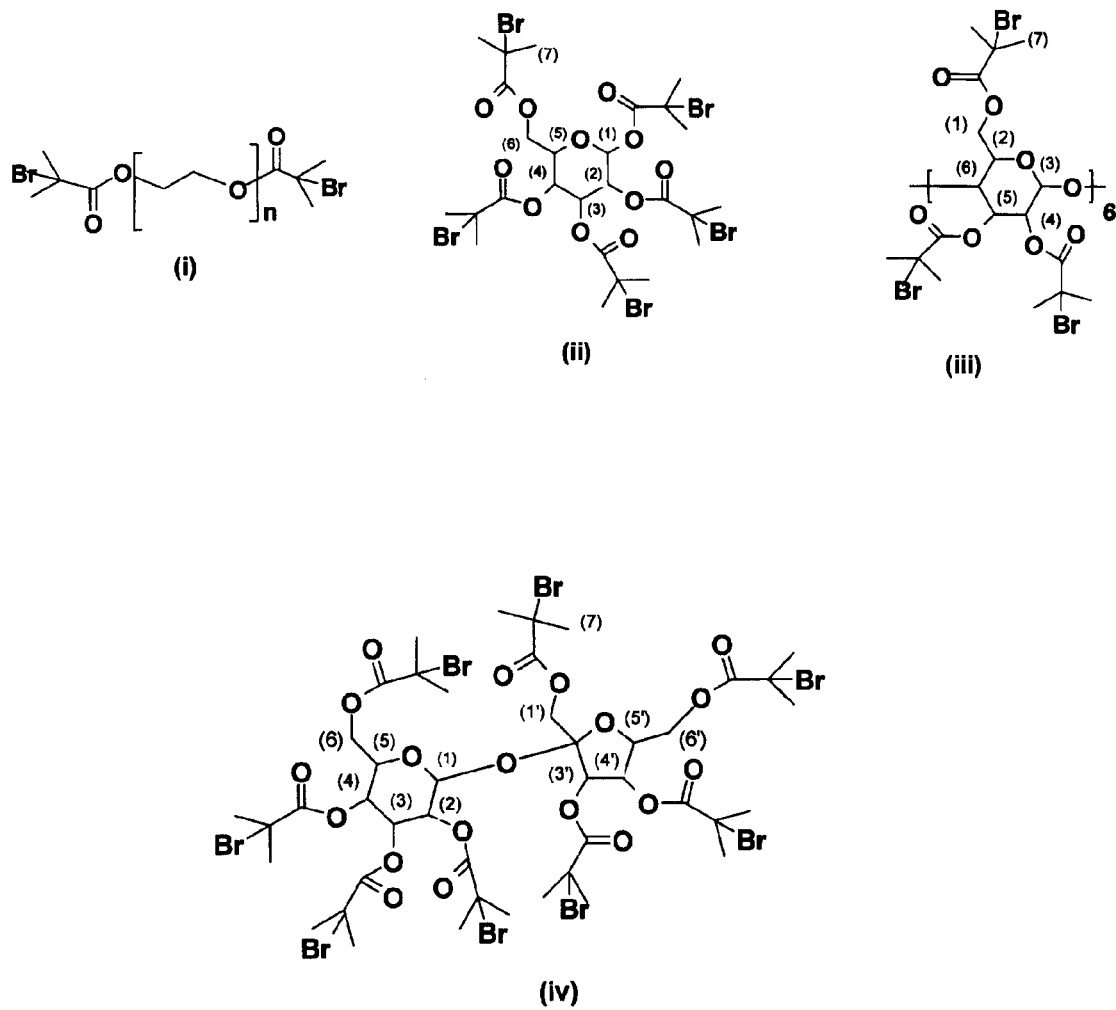
FIG. 1 presents the chemical structures of linear and multifunctional ATRP initiators used to synthesize polymers described herein. (i) PEG-dibromo macroinitiator; (ii) 1,2,3,4,6-penta-O-isobutyryl bromide-R-D-Glucose; (iii) Octadeca-O-isobutyryl bromide-R-cyclodextrin; (iv) Octa-O-isobutyryl bromide-sucrose.

Atom transfer radical polymerization (ATRP) initiators (FIG. 1) were prepared from PEG, R-D-glucose, sucrose and α-cyclodextrin. The bromide functionalization of the last three molecules was achieved by the approach described by Stenzel-Rosenbaum and co-workers (22).

The present invention is illustrated in further details by the following non-limiting examples.

Example 1

Synthesis of PEG Dibromomacroinitiator (i)

A solution of HO-PEG-OH ($M_n$ 2000, 10 g, 5 mmol) and triethylamine (10 g, 0.1 mol) in 70 mL of anhydrous toluene was slightly cooled in an ice-water bath. Then, 2-bromoisobutyryl bromide (4.91 mL, 0.04 mol) was slowly added to the reaction mixture. The solution was warmed to room temperature and stirred for 48 h. The mixture was filtered, half of the solvent was evaporated, and the PEG macroinitiator was precipitated in cold diethyl ether (FIG. 1 (i)).

Yield: 90%, after precipitation. White solid. $^1$H NMR (δ, ppm, CDCl$_3$): 3.50 (188H), 1.80 (12H, s).

Example 2

Synthesis of 1,2,3,4,6-Penta-O-isobutyryl bromide-R-D-glucose (ii)

2-bromoisobutyryl bromide (50 g, 0.22 mol) was slowly added to a solution of R-D-glucose (5.0 g, 0.028 mol) in an anhydrous mixture of chloroform (100 mL) and pyridine (50 mL). The solution was refluxed for 3 h while maintaining a dry atmosphere and then stirred at room temperature for a further 12 h. It was then washed successively with ice-cold water, NaOH (0.1 M), and water and dried over anhydrous MgSO$_4$. The crude product was recrystallized from methanol to yield white crystals (FIG. 1 (ii)).

Yield: 70%. $^1$H NMR (CDCl$_3$): 1.85-2.04 (m, 30H, H-7), 6.42 (d, 1H, H-1), 5.25 (dd, 1H, H-2), 5.69 (t, 1H, H-3), 5.35 (t, 1H, H-4), 4.38 (m, 3H, H-5/6).

Example 3

Synthesis of Octadeca-O-isobutyryl Bromide-R-cyclodextrin (iii)

Octadeca-O-isobutyryl bromide-R-cyclodextrin was synthesized by the slow addition of 2-bromoisobutyryl bromide (50 g, 0.22 mol) to a solution of R-cyclodextrin (5.0 g, 0.005 mol) in anhydrous pyridine (150 mL). The solution was stirred for 24 h under a dry atmosphere at room temperature. It was then washed with ice-cold water, NaOH (0.1 M), and water, respectively, prior to drying over anhydrous MgSO$_4$. The crude product was recrystallized from methanol/H$_2$O (3:1, v/v) to yield white crystals (FIG. 1 (iii)).

Yield: 55%. $^1$H NMR (CDCl$_3$): 1.95 (m, 108H, H-7), 5.84 (d, 12H, H-1), 4.46 (dd, 6H, H-2), 5.7 (m, 6H, H-3), 5.13/5.38 (t/dd, 6H, H-4), 4.78 (dd, 6H, H-5), 4.45 (m, 6H, H-6).

Example 4

Synthesis of Octa-O-isobutyryl bromide-sucrose (iv)

Octa-O-isobutyryl bromide sucrose was synthesized by the slow addition of 2-bromoisobutyryl bromide (50 g, 0.22 mol) to a solution of sucrose (5.0 g, 0.014 mol) in anhydrous pyridine (150 mL). The solution was stirred for 24 h under a dry atmosphere at room temperature. It was then washed with ice-cold water, NaOH (0.1 M), and water, prior to drying over anhydrous $MgSO_4$. The crude product was recrystallized from methanol/$H_2O$ (3:1 v/v) to yield white crystals (FIG. 1 (vi)).

Yield: 50%. $^1$H NMR ($CDCl_3$): 1.99 (m, 48H, H-7), 4.15 (d, 1H, H-5'), 4.46 (m, 5H, H-6'/1'/5), 4.68 (dt, 2H, H-6), 4.81 (d, 1H, H-3'), 5.13 (dd, 1H, H-2), 5.38 (t, 1H, H-4'), 5.67 (t, 1H, H-4), 5.76 (t, 1H, H-3), 5.85 (d, 1H, H-1).

Example 5

Synthesis of Linear Hydroxyethyl Methacrylate (HEMA)/4-Styrene Sulfonic Acid Sodium Salt Hydrate (SStNA) Copolymer (93.5/6.5 mol % after Purification)

The ATRP initiator i (FIG. 1) (50 mg), SStNa (0.375 g) and HEMA (7.12 g) were dissolved in 46 mL of a methanol/water (1/4) mixture and degassed under argon for 15 min. Bpy (20.28 mg), Cu(I)Br (7.2 mg) and Cu(II)$Br_2$ (3.35 mg) were then added under stirring at 20° C. After 24 h, the solution was exposed to air and the dark-brown solution turned to blue, indicating oxidation of Cu(I) to Cu(II). The polymer was purified by passing the methanol/water solution through a silica gel column which removed the Cu(II) catalyst. The polymers were dialyzed (Spectra/Por™ no. 1, MW cutoff 6000-8000, Spectrum Laboratories, Rancho Dominguez, Calif.) against water for 48 h and then freeze-dried until use. $M_w$=318 700 g/mol; $M_w/M_n$=2.54.

Example 6

Synthesis of Linear Hydroxyethyl Methacrylate/4-Styrene Sulfonic Acid Sodium Salt Hydrate Copolymer (90.3/9.7 mol % after Purification)

The ATRP initiator i (FIG. 1) (50 mg), SStNa (0.375 g) and HEMA (7.12 g) were dissolved in 46 mL of a methanol/water (1/4) mixture and degassed under argon for 15 min. Bpy (21.84 mg), Cu(I)Br (7.2 mg) and Cu(II)$Br_2$ (4.48 mg) were then added under stirring at 20° C. After 24 h, the solution was exposed to air and the polymer was purified as reported in Example 5. $M_w$=331 528, $M_w/M_n$=2.9

Example 7

Synthesis of Linear Hydroxyethyl Methacrylate/4-Styrene Sulfonic Acid Sodium Salt Hydrate Copolymer (87.8/12.2 mol % after Purification)

The ATRP initiator i (FIG. 1) (50 mg), SStNa (0.75 g) and HEMA (6.747 g) were dissolved in 46 mL of a methanol/water (1/4) mixture and degassed under argon for 15 min. Bpy (15.6 mg) and Cu(I)Br (7.2 mg) were then added under stirring at 20° C. After 24 h, the solution was exposed to air and the polymer was purified as reported in Example 5. $M_w$=283 600 g/mol; $M_w/M_n$=2.57.

Example 8

Synthesis of Linear Hydroxyethyl Methacrylate/4-Styrene Sulfonic Acid Sodium Salt Hydrate Copolymer (82.4/17.6 mol % after Purification)

The ATRP initiator i (FIG. 1) (50 mg), SStNa (1.125 g) and HEMA (6.426 g) were dissolved in 46 mL of a methanol/water (1/4) mixture and degassed under argon for 15 min. Bpy (15.6 mg) and Cu(I)Cl (5 mg) were then added under stirring at 20° C. After 24 h, the solution was exposed to air and the polymer was purified as reported in Example 5. $M_w$=275 500 g/mol; $M_w/M_n$=2.5.

Example 9

Synthesis of Linear Hydroxyethyl Methacrylate/4-Styrene Sulfonic Acid Sodium Salt Hydrate Copolymer (69/31 mol % after Purification)

The ATRP initiator i (FIG. 1) (50 mg), SStNa (1.5 g) and HEMA (5.99 g) were dissolved in 46 mL of a methanol/water (1/4) mixture and degassed under argon for 15 min. Bpy (15.6 mg) and Cu(I)Cl (5 mg) were then added under stirring at 20° C. After 24 h, the solution was exposed to air and the polymer was purified as reported in Example 5. $M_w$=NA; $M_w/M_n$=NA. $Mn_{(NMR)}$=58 100 g/mol.

Example 10

Synthesis of Linear Hydroxyethyl Methacrylate/4-Styrene Sulfonic Acid Sodium Salt Hydrate Copolymer (51.5/48.5 mol % after Purification)

The ATRP initiator i (FIG. 1) (50 mg), SStNa (3.2 g) and HEMA (3.95 g) were dissolved in 46 mL of a methanol/water (1/4) mixture and degassed under argon for 15 min. Bpy (15.6 mg) and Cu(I)Br (7.2 mg) were then added under stirring at 20° C. After 24 h, the solution was exposed to air and the polymer was purified as reported in Example 5. $M_w$=122 000 g/mol; $M_w/M_n$=2.23.

Example 11

Synthesis of Linear Hydroxyethyl Methacrylate/4-Styrene Sulfonic Acid Sodium Salt Hydrate Copolymer (43/57 mol % after Purification)

The ATRP initiator i (FIG. 1) (50 mg), SStNa (2.4 g) and HEMA (1 g) were dissolved in 23 mL of a methanol/water (1/4) mixture and degassed under argon for 15 min. Bpy (15.6 mg) and Cu(I)Br (7.2 mg) were then added under stirring at 20° C. After 24 h, the solution was exposed to air and the polymer was purified as reported in Example 5. $Mn_{(NMR)}$=55 000 g/mol.

Example 12

Synthesis of Linear Hydroxyethyl Methacrylate/4-Styrene Sulfonic Acid Sodium Salt Hydrate Copolymer (28/72 mol % after Purification)

The ATRP initiator i (FIG. 1) (50 mg), SStNa (4.8 g) and HEMA (1.975 g) were dissolved in 46 mL of a methanol/ water (1/4) mixture and degassed under argon for 15 min. Bpy (15.6 mg) and Cu(I)Br (7.2 mg) were then added under stirring at 20° C. After 24 h, the solution was exposed to air and the polymer was purified as reported in Example 5. $M_w$=65 200 g/mol; $M_w/M_n$=1.95.

Example 13

Synthesis of Linear Poly(4-Styrene Sulfonic Acid Sodium Salt Hydrate)

The ATRP initiator i (FIG. 1) (50 mg) and SStNa (6.4 g) were dissolved in 46 mL of water and degassed under argon for 15 min. Bpy (15.6 mg) and Cu(I)Br (7.2 mg) were then added under stirring at 20° C. After 24 h, the solution was exposed to air and the polymer was purified as reported in Example 5. $M_w$=NA; $M_w/M_n$=NA. $M_{n\ (NMR)}$=20 000 g/mol.

Example 14

Synthesis of Linear Poly(4-Styrene Sulfonic Acid Sodium Salt Hydrate)

The ATRP initiator i (FIG. 1) (50.3 mg) and SStNa (1.56 g) were dissolved in 20 mL of water and degassed under argon for 15 min. Bpy (15.6 mg) and Cu(I)Br (7.2 mg) were then added under stirring at 20° C. After 24 h, the solution was exposed to air and the polymer was purified as reported in Example 5. $M_w$=NA; $M_w/M_n$=NA. $M_{n\ (NMR)}$=57 500 g/mol.

Example 15

Synthesis of 5-Arm Star Hydroxyethyl Methacrylate/4-Styrene Sulfonic Acid Sodium Salt Hydrate Copolymer (69/31 mol % after Purification)

The ATRP initiator ii (FIG. 1) (142.6 mg), SStNa (1.55 g) and HEMA (4.616 g) were dissolved in 30 mL of a methanol/water (8/1) mixture and degassed under argon for 15 min. Bpy (230.75 mg) and Cu(I)Br (106 mg) were then added under stirring at 20° C. After 1 h of reaction, 10 mL of water were added and the solution was then maintained at room temperature for 24 h. The corresponding copolymer was finally purified as reported in Example 5. $M_w$=85 000 g/mol; $M_w/M_n$=1.79.

Example 16

Synthesis of 8-Arm Star Hydroxyethyl Methacrylate/4-Styrene Sulfonic Acid Sodium Salt Hydrate Copolymer (75/25 mol % after Purification)

The ATRP initiator iv (FIG. 1) (141 mg), SStNa (1.5 g) and HEMA (4.616 g) were dissolved in 30 mL of a methanol/water (8/1) mixture and degassed under argon for 15 min. Bpy (230.8 mg) and Cu(I)Br (106 mg) were then added under stirring at 20° C. After 1 h of reaction, 10 mL of water were added and the solution was then maintained at room temperature for 24 h. The corresponding copolymer was finally purified as reported in Example 5. $M_w$=210 000 g/mol; $M_w/M_n$=2.03.

Example 17

Synthesis of 18-Arm Star Hydroxyethyl Methacrylate/4-Styrene Sulfonic Acid Sodium Salt Hydrate Copolymer (69/31 mol % after Purification)

The ATRP initiator iii (FIG. 1) (153.5 mg), SStNa (1.5 g) and HEMA (4.62 g) were dissolved in 30 mL of a methanol/water (8/1) mixture and degassed under argon for 15 min. Bpy (230.75 mg) and Cu(I)Br (106 mg) were then added under stirring at 20° C. After 1 h of reaction, 10 mL of water were added and the solution was then maintained at room temperature for 24 h. The corresponding copolymer was finally purified as reported in Example 5. $M_w$=206 000 g/mol; $M_w/M_n$=2.6.

Example 18

Synthesis of Linear Hydroxyethyl Methacrylate (HEMA)/Sulfopropyl Methacrylate Potassium Salt (SPMAK) Copolymer (86114 mol % after Purification)

The ATRP initiator i (FIG. 1) (100.3 mg), SPMAK (1.85 g) and HEMA (5.62 g) were dissolved in 30 mL of methanol and degassed under argon for 15 min. Bpy (31.96 mg) and Cu(I)Br (15.1 mg) were then added under stirring at 20° C. After 24 h, the solution was exposed to air and the polymer was purified as reported in Example 5. $M_w$=NA; $M_w/M_n$=NA. $M_{n\ (NMR)}$=66 500 g/mol.

Example 19

Synthesis of Linear Hydroxyethyl Methacrylate (HEMA)/Sulfopropyl Methacrylate Potassium Salt (SPMAK) Copolymer (83/17 mol % after Purification)

The ATRP initiator i (FIG. 1) (102.1 mg), SPMAK (1.90 g) and HEMA (5.62 g) were dissolved in 30 mL of methanol and degassed under argon for 15 min. Bpy (31.24 mg) and Cu(I)Br (14.34 mg) were then added under stirring at 20° C. After 24 h, the solution was exposed to air and the polymer was purified as reported in Example 5. $M_w$=NA; $M_w/M_n$=NA. $M_{n\ (NMR)}$=84 000 g/mol.

Example 20

Synthesis of Linear Hydroxyethyl Methacrylate/Sulfopropyl Methacrylate Potassium Salt Copolymer (74/26 mol % after Purification)

The ATRP initiator i (FIG. 1) (100.5 mg), SPMAK (3.75 g) and HEMA (5.622 g) were dissolved in 46 mL of a methanol/water (1/1) mixture and degassed under argon for 15 min. Bpy (32 mg) and Cu(I)Br (15.1 mg) were then added under stirring at 20° C. After 24 h, the solution was exposed to air and the polymer was purified as reported in Example 5. $M_w$=NA; $M_w/M_n$=NA. $M_{n\ (NMR)}$=119 000 g/mol.

Example 21

Synthesis of Linear Hydroxyethyl Methacrylate/Sulfopropyl Methacrylate

Potassium Salt Copolymer (45/55 mol % after purification)
The ATRP initiator i (FIG. 1) (100.7 mg), SPMAK (5.64 g) and HEMA (1.752 g) were dissolved in 46 mL of a methanol/water (1/1) mixture and degassed under argon for 15 min. Bpy (32 mg) and Cu(I)Br (15.1 mg) were then added under stirring at 20° C. After 24 h, the solution was exposed to air and the polymer was purified as reported in Example 5. $M_w$=NA; $M_w/M_n$=NA. $Mn_{(NMR)}$=108 500 g/mol.

Example 22

Synthesis of Linear Poly(Sulfopropyl Methacrylate Potassium)

The ATRP initiator i (FIG. 1) (100.7 mg) and SPMAK (7.5 g) were dissolved in 46 mL of a methanol/water (1/1) mixture and degassed under argon for 15 min. Bpy (32 mg) and Cu(I)Br (15.1 mg) were then added under stirring at 20° C. After 24 h, the solution was exposed to air and the polymer was purified as reported in Example 5. Mw=NA; Mw/Mn=NA. Mn (NMR)=120 000 g/mol.

Example 23

Synthesis of 5-Arm Star Hydroxyethyl Methacrylate/Sulfopropyl Methacrylate Potassium Copolymer (82.4/17.6 mol % after Purification)

The ATRP initiator ii (FIG. 1) (143 mg), SPMAK (1.87 g) and HEMA (4.61 g) were dissolved in 60 mL of a methanol/water (8/1) mixture and degassed under argon for 15 min. Bpy (230.6 mg) and Cu(I)Br (108 mg) were then added under stirring at 20° C. After 24 h, the solution was exposed to air and the polymer was purified as reported in Example 5. $M_w$=161 000 g/mol; $M_w/M_n$=2.4.

Example 24

Synthesis of 8-Arm Star Hydroxyethyl Methacrylate/Sulfopropyl Methacrylate Potassium Copolymer (81/19 mol % after Purification)

The ATRP initiator iv (FIG. 1) (70.5 mg), SPMAK (0.935 g) and HEMA (2.3 g) were dissolved in 60 mL of a methanol/water (8/1) mixture and degassed under argon for 15 min. Bpy (115.8 mg) and Cu(I)Br (53.9 mg) were then added under stirring at 20° C. After 24 h, the solution was exposed to air and the polymer was purified as reported in Example 5. $M_w$=227 000 g/mol; $M_w/M_n$=2.27.

Example 25

Synthesis of 18-Arm Star Hydroxyethyl Methacrylate/Sulfopropyl Methacrylate Potassium Copolymer (82.4/17.6 mol % after purification)

The ATRP initiator iii (FIG. 1) (75.3 mg), SPMAK (0.923 g) and HEMA (2.31 g) were dissolved in 60 mL of a methanol/water (8/1) mixture and degassed under argon for 15 min. Bpy (115.8 mg) and Cu(I)Br (53.9 mg) were then added under stirring at 20° C. After 24 h, the solution was exposed to air and the polymer was purified as reported in Example 5. $M_w$=342 000 g/mol; $M_w/M_n$=2.28.

Example 26

Assessment of Polymer-Gliadin Binding

The binding selectivity and affinity of gliadin toward the synthesized polymers was assessed by sodium dodecyl sulfate polyacrylamide gel electrophoresis (SDS-PAGE) using a 15% (w/v) separating gel. In addition, the polymers were separately screened for their reactivity toward control proteins, namely bovine albumin and/or bovine casein. Binding studies were carried out at pH 1.2 and 6.8 using hydrochloric acid and phosphate buffers, respectively. Polymer (80 mg/L) and protein (40 mg/L) were mixed together at pHs 1.2 and 6.8 and incubated for 2 h. The solutions were then centrifuged at 15 000 g for 30 min in order to separate the insoluble complex from free protein that remained in solution. The supernatant was then analyzed by SDS-PAGE to measure the amount of free protein.

Example 27

Selectivity of Poly(HEMA-Co-SStNa) Binding to Gliadin

Figure 2:
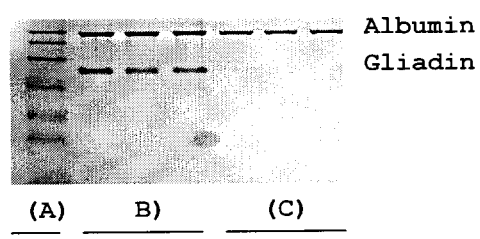
FIG. 2 presents the SDS-PAGE of the binding of albumin and α-gliadin with poly(HEMA-co-SStNa) (Example 10) at pH 6.8 in triplicate: (A) protein standards; (B) albumin and α-gliadin mixture; (C) mixture of albumin (40 mg/L), α-gliadin (40 mg/L) and poly(HEMA-co-SStNa) (160 mg/L)
Figure 3:
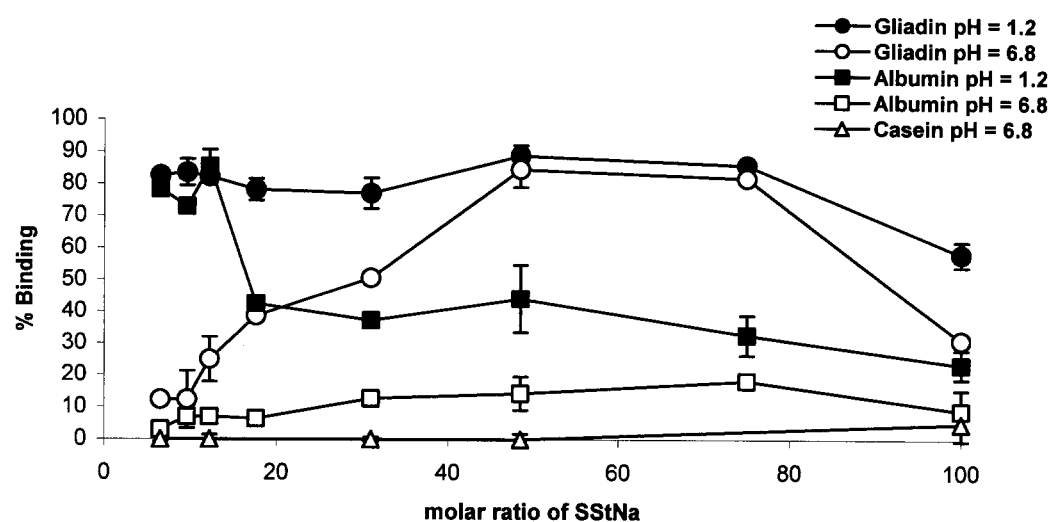
FIG. 3 is a binding profile of linear poly(HEMA-co-SStNa) to gliadin, albumin, and casein at pH 1.2 and 6.8, wherein each point corresponds to the polymer of each of Examples 5 to 10 and 12-13.

The binding affinity of gliadin toward different linear poly (HEMA-co-SStNa) (synthesis reported in Examples 5 to 10 and 12-14) was assessed by SDS-PAGE as described in Example 26 and compared to that of albumin and casein (FIG. 3 showing Examples 5 to 10 and 12-13) at intestinal (6.8) and gastric (1.2) pHs. In general, the polymer exhibited greater affinity for gliadin compared to the control proteins at both pH values. It has to be pointed out that the complexation with casein was not studied at pH 1.2 due to the insolubility of this protein under acidic conditions. As shown by FIG. 3, complexation to gliadin could be modulated by the copolymer composition. FIG. 2 also shows selective binding on SDS-PAGE between gliadin and linear poly(HEMA-co-SStNa) (Example 10), whereas albumin remained free in solution upon incubating the copolymer with both proteins. The binding affinity of gliadin toward the linear poly(HEMA-co-SStNa) polymer of Example 14 was assessed by SDS-PAGE as described in Example 26 and compared to that of albumin. Results were as follows: complexation with albumin at pHs 1.2 and 6.8 was of 78.8% and 11.23%, respectively; complexation with gliadin at pHs 1.2 and 6.8 was of 100% and 71.3%, respectively.

Example 28

Selectivity of Poly(HEMA-co-SPMAK) Composition Binding to Gliadin

Figure 4:
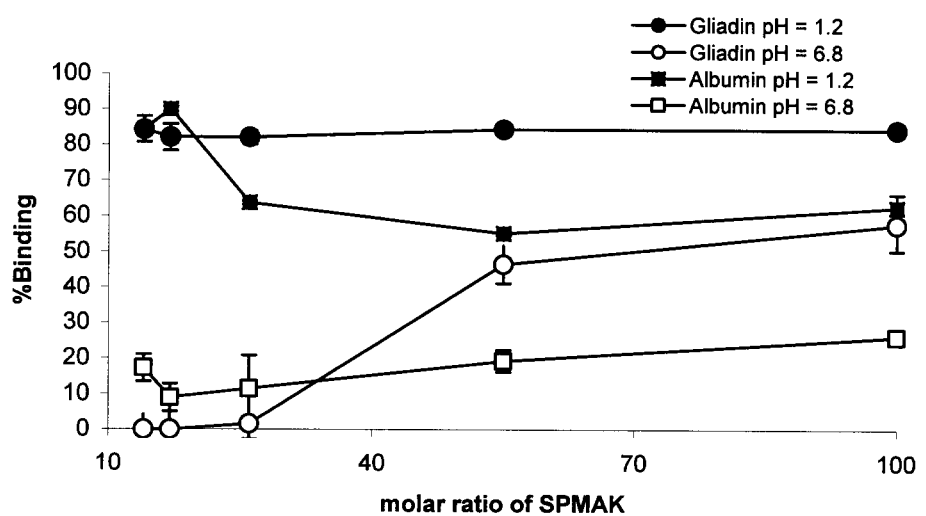
FIG. 4 is a binding profile of linear poly(HEMA-co-SPMAK) to gliadin and albumin at pH 1.2 and 6.8 wherein each point corresponds to the polymer of each of Examples 17 to 21.

The binding affinity of gliadin toward different linear poly (HEMA-co-SPMAK) (synthesis reported in Examples 18 to 22) was assessed by SDS-PAGE as described in Example 26 and compared to that of albumin (FIG. 4) at intestinal (6.8) and gastric pHs (1.2). Lesser binding to gliadin was observed when the SStNa monomer was replaced by SPMAK especially at pH 6.8 (FIG. 4). Optimal complexation to gliadin was achieved for SPMAK ratios ranging from 50 to 100 mol %.

Example 29

Effect of Copolymer Structure on Binding to Gliadin

Figure 5:
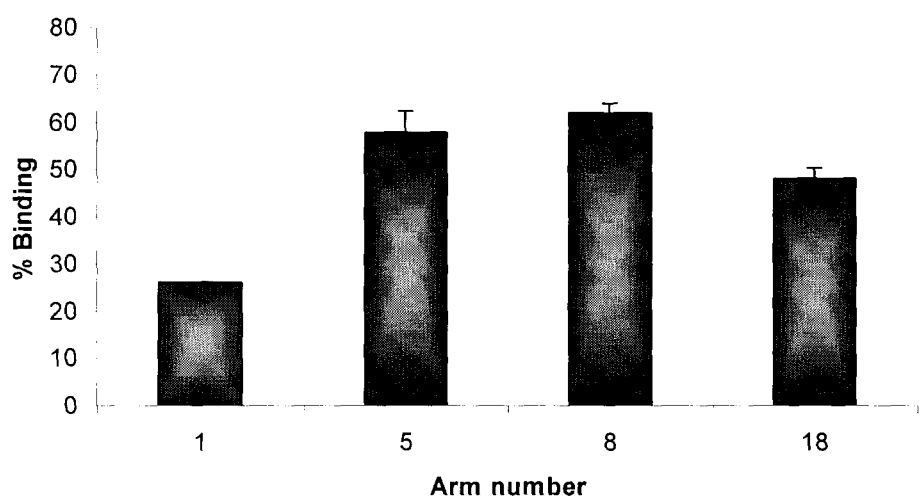
FIG. 5 graphically presents the polymer structure effect on the binding of gliadin at neutral pH (SStNa=25-31 mol %; see Examples 9, 14, 15 and 16)
Figure 6:
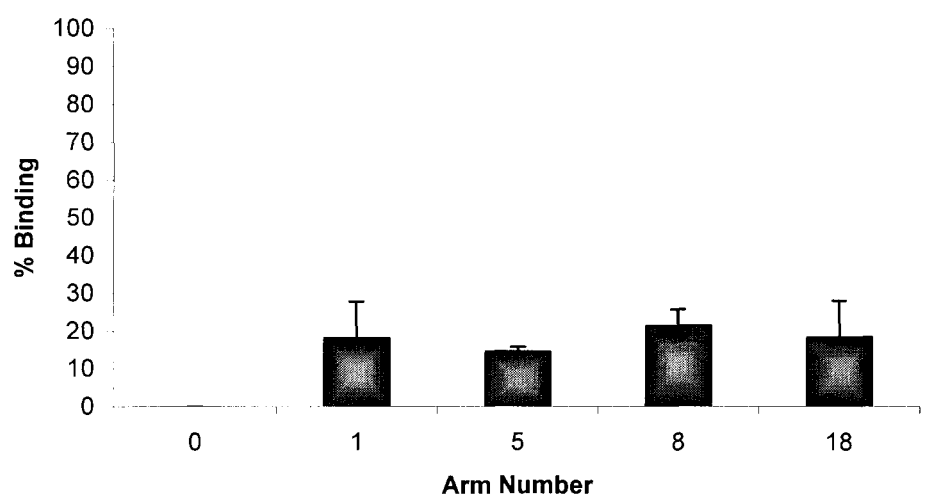
FIG. 6 graphically presents the polymer structure effect on the binding of gliadin at neutral pH (SPMAK=16-19 mol %; see Examples 18, 22, 23 and 24)

Five, eight and eighteen arms star poly(HEMA-co-SStNa) (Examples 15 to 17) and poly(HEMA-co-SPMAK) (Examples 23 to 25) were synthesized using initiators derived from glucose, sucrose and cyclodextrin, respectively. Their ability to bind gliadin was compared to their linear counterpart (Examples 9 and 18, respectively). The results are presented in FIGS. 5 and 6. For a fixed percentage of SStNa of about 30 mol %, the binding efficiency of eight arms star poly(HEMA-co-SStNa) was better than the linear or the other star copolymers (FIG. 5). At a fixed ratio of SPMAK of 17 mol %, no significant difference was observed in the binding of gliadin to linear or star poly(HEMA-co-SPMAK) (FIG. 6).

Conclusions

Linear and star-shaped random copolymers of HEMA and SStNa or SPMAK were shown to bind α-gliadin under pH conditions mimicking the gastrointestinal tract.

Example 30

Effect of Copolymer Molecular Weight on Binding to Gliadin

Figure 9:
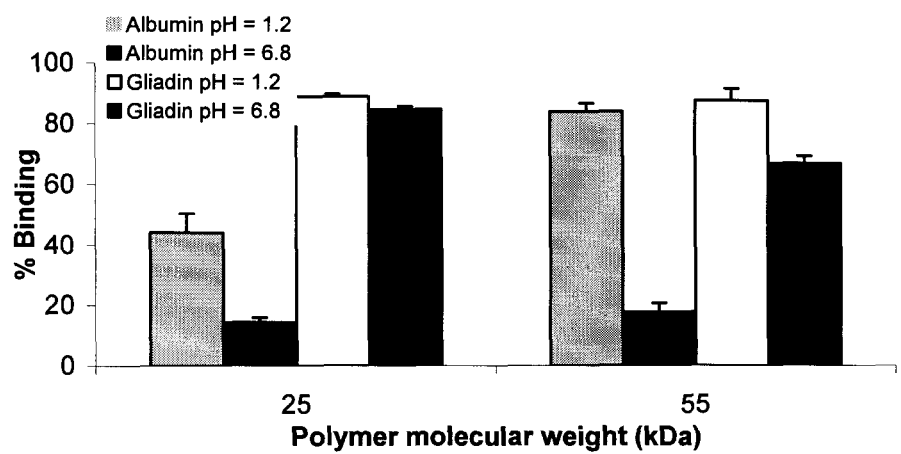
FIG. 9 presents a binding profile of two linear poly(HEMA-co-SStNa) containing about 50% SStNa and having two different molecular weights (Examples 10 and 11) to gliadin and albumin at pH 1.2 and 6.8.

Two different weights linear poly(HEMA-co-SStNa) (Examples 10 and 11) containing about 50% SStNa were tested for the binding of gliadin and albumin at both pHs 1.2 and 6.8. In this experience, each protein was tested separately. The results are presented in FIG. 9. The binding to gliadin and selectivity of binding was found to be influenced by the molecular weight of the polymer.

Example 31

Prevention of Enzymatic Degradation of Gliadin by a Copolymer

Preparation of Peptic-Tryptic Digests of Gliadin

The stepwise enzymatic hydrolysis of α-gliadin was performed with pepsin (Sigma P0609; St Louis, Mo., USA) and trypsin (Sigma T1763), both attached to agarose as well as α-chymotrypsin from bovine pancreas (Sigma C4129). α-Gliadin (10 mg) was dissolved in 5 mL of hydrochloric acid buffer pH=1.2 (10 mM) and pepsin (38 U) was added. The mixture was magnetically stirred at 37° C. for 2 hours at which point the pH was adjusted to 6.8 with 0.1 mol/L NaOH and trypsin (0.75 U) as well as α-chymotrypsin (0.5 U) were added. The digest was centrifuged for 30 min at 20° C. and 6000 g. The gliadin peptides were thereafter collected in the supernatant and filtered through 0.2 μm GHP filters.

The resulting peptic-tryptic-chymotryptic digest of gliadin was analyzed using a Waters™ high-performance liquid chromatography HPLC system equipped with a 1525 Binary pump, a 2487 dual wavelength absorbance detector, and a Breeze Chromatography Software™ (Waters, Midford, Mass.). Samples were eluted at 36° C. at a flow rate, detection wavelength, and injection volume of 1 mL/min, 215 nm and 50 μL, respectively. Trifluoroacetic acid was used as an ion pairing agent, and elution was performed with a linear gradient consisting of 100% buffer A to 100% buffer B spanning over 60 min. Buffer A consisted of 0.1% trifluoroacetic acid, 95% water, and 5% acetonitrile and buffer B consisted of 0.1% trifluoroactic acid, 5% water, and 95% acetonitrile. A portion of each sample supernatant was diluted into water and analysed on a $C_{18}$ reversed phase column (Waters Novapack™ C18, 60 Å, 4 μm, 3.9×300 mm).

Enzymatic Degradation of the Gliadin-Polymer Complex

Poly(HEMA-co-SStNa) (Example 10) (4 g/L) and gliadin (2 g/L) were mixed together at pH 2 and incubated for 2 h. Then, the stepwise enzymatic degradation of gliadin-polymer complex was performed as described above. The effect of the polymeric binder on the degradation of gliadin was analysed using HPLC as described above (FIG. 7).

Figure 7:
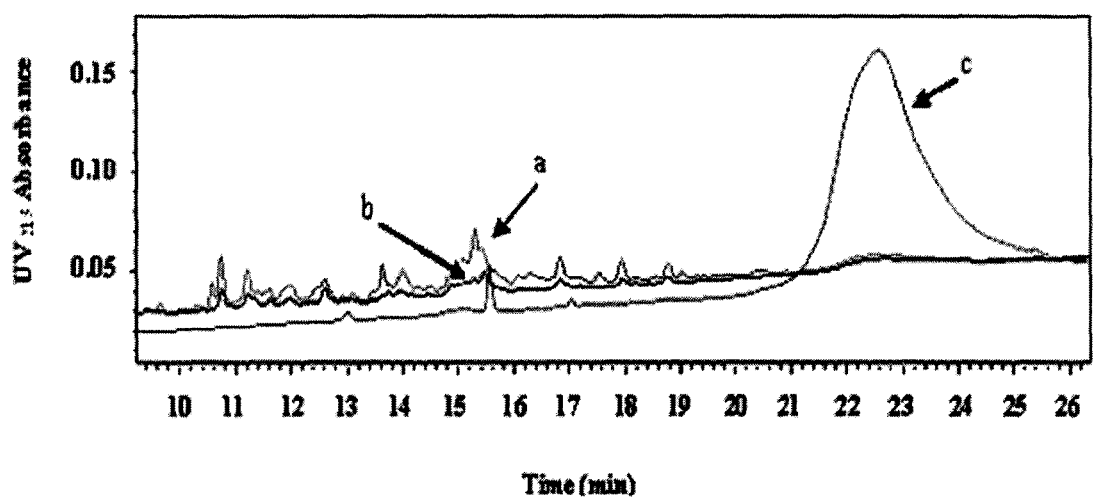
FIG. 7 presents the effect of a polymer of the invention on gliadin digestion under simulated intestinal conditions. Comparative HPLC profiles of gliadin digested with pepsin, trypsin and chymotrypsin (PTC) in absence (a) and presence (b) of polymer. Chromatogram (c) corresponds to intact α-gliadin.

Substantially less degradation products were detected when the gliadin was complexed to the polymer (FIG. 7).

Example 32

Effect of Polymer Polymer on Caco-2 Monolayer Integrity

Figure 8:
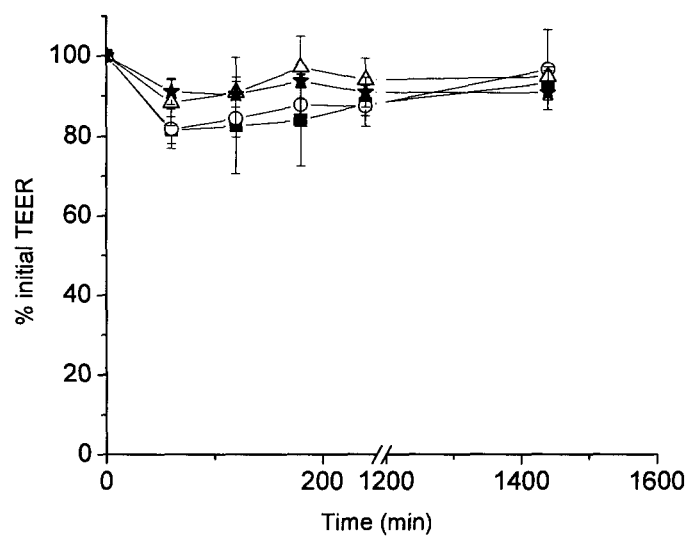
FIG. 8 presents the variation of the transepithelial electric resistance (TEER) of a Caco-2 monolayer following incubation with solutions of PEG ($M_n$: 35,000; open circles), PVP ($M_w$: 58,000; closed squares), poly(HEMA-co-SStNa) (Example 10; open triangles) and complete medium (closed stars) as a control. Cells were maintained in DMEM cell culture media supplemented with 10% FBS. The polymer concentration was fixed at 1 g/L.

The effect of poly(HEMA-co-SStNa) (Example 10) on Caco-2 cell monolayer integrity was assessed and compared to that of PEG (35 kDa) and PVP (58 kDa) (FIG. 8). Cells were seeded onto 12-well Transwell® polycarbonate filters (Corning, Acton, Mass.) at a seeding density of $2.5 \times 10^5$ cell/$cm^2$. Caco-2 were grown in Dulbecco's modified essential medium (DMEM) supplemented with 10% (v/v) foetal bovine serum, non-essential amino acid solution (0.1 mM), Hepes buffer pH 7.4 (10 mM) and penicillin-streptomycin (eq. 100 U/mL and 100 μg/mL). Medium was refreshed every 72 h. Cells were cultured for 21-28 days at 37° C., 5% $CO_2$ to form a differentiated monolayer prior to the experiments. Toxicity studies were performed in complete DMEM medium. Transepithelial electrical resistance (TEER) readings were taken at pre-determined time-points using a Millicell™ Electrical Resistance System (Millipore Corp. Bedford, Mass.) with a single electrode (World Precision Instruments, Sarasota, Fla.).

In both the Poly(HEMA-co-SStNa) and control polymers (PVP, PEG), the TEER measured after 24 hours showed a reduction of 10% of the initial value (FIG. 8). These results indicate that Poly(HEMA-co-SStNa) do not seem to strongly perturb the integrity of the Caco-2 cell monolayer.

Example 33

In Vivo Testing of Effect of Polymeric Binder on Reduction of Toxicity of Gliadin and Gliadin Degradation Products The ability of the polymer to reduce the toxicity of gluten is evaluated in vivo by measuring the immune response of animals that have been sensitized to gluten or its degradation products. The immune response is measured in transgenic mice expressing HLA-DQ8 (24) following oral administration of gluten or its degradation products in the presence or absence of polymeric binder.

Example 34

Incorporation of Polymeric Binder in Food

The polymeric binder may be incorporated into gluten-containing food directed to individuals affected by celiac disease. The polymeric binder in such food may then counteract the deleterious effects of the gluten contained in the food when it is swallowed. Without being so limited, such food includes ready-cooked dishes, cereals, baked goods such bread, pastry, pies, cakes, muffins, cookies etc. Such food may incorporate the polymeric binder in a concentration of 0.01% to 10% (w/w). The polymeric binder can also be incorporated into non gluten-containing food for consumption in a meal containing gluten-containing food. Without being so limited, such non gluten-containing food includes spreads such as cheese, jams, butter or any food that can be eaten on or with gluten-containing food.

Although the present invention has been described hereinabove by way of specific embodiments thereof, it can be modified, without departing from the spirit and nature of the subject invention as defined in the appended claims.

REFERENCES

1. Sollid L. M. (2002) *Nat Rev Immunol* 2, 647-655.
2. Shan L., Molberg O, Parrot I., Hausch F., Filiz F., Gray G. M., Sollid L. M., Kholsa C. (2002) *Science* 297, 2275-2279.
3. Charles H. Halsted, M D, "The Many Faces of Celiac Disease" (1996) *New England Journal of Medicine*, May 2, 1996—Volume 334, Number 18.

4. Trier J S. Celiac sprue. (1991) *N England J Med;* 325; 1709-1719.
5. Ciacci, C., Cirillo, M., Cavallaro, R. & Mazzacca, G. (2002) *Digestion* 66, 178-185.
6. F., Shan, L., Santiago, N. A., Gray, G. M. & Khosla, C. (2002) *Am. J. Physiol. Gastrointest. Liver Phyiol.* 283, G996-G 003.
8. Kim C. Y., Quarsten H., Bergseng E., Kholsa C., Sollid L. M. (2004) *PNAS* 101, 12, 4175-4179.
9. Fasano A., Not T., Wang W., Uzzau S., Berti I., Tommasini A., Goldblum S. E. (2000), *The Lancet* 355, 1518-1519.
10. Molberg et al. (2005) *Gastroenterology,* 128, 393-401.
11. Vader L. W. et al. (2003) *Gastroenterology,* 125, 1105-1113.
12. Sollid L. M., Kholsa C. (2005) *Nat Clin Pract Gastroenterol Hepatol.* 2 (3), 140-147.
13. Kurtz, C. B., Cannon, E. P., Brezzani, A., Pitruzello, M., Dinardo, C., Rinard, E., Acheson, D. W. K., Fitzpatrick, R., Kelly, P., Shackett, K., Papoulis, A. T., Goddard, P. J., Barker Jr, R. H., Palace, G. P. & Klinger, J. D. (2001) *Antimicrob. Agents Chemother.* 45, 2340-2347.
14. Auricchio, S., De Ritis, G., De Vincenzi, M., Magazzù, G., Maiuri, L., Mancini, E., Minetti, M., Sapora, O. & Silano, V. (1990) *Gastroenterology* 99, 973-978.
15. Mothes, T. & Stern, M. (2003) *Eur. J. Gastroenterol. Hepatol.* 15, 461-463.
16. Popineau, Y., Lefebvre, J., Godon, B., (1980) *Ann Technol. Agric.* 29 (2), 191-204.
17. Popineau, Y., Godon, B., (1982) *Cereal Chemistry* 59 (1), 55-62.
18. Godon, B., Leblanc, M. P., Popineau, Y., (1983) *Qual. Plant Foods Hum. Nutr* 33, 161-168.
19. Popineau, Y., (1985) *J Cereal Sci,* 3, 29-38.
20. Popineau, Y., Pineau, F., (1985) *Lebensm-Wiss.u.Technol.* 18, 133-135.
21. Popineau, Y., Le Guerroue, J. L., (1991) *J Cereal Sci,* 14, 231-241.
22. Stenzel-Rosenbaum, M., Davis, T. P., Chen, V., Fane, A. G. (2001) *Macromolecules* 34, 5433-5438.
23. Ciccocioppo, R., et al. (2005) *Clin. Exp. Immunol.,* 140: 408-416.
24. Senger S., Luongo D., (2003) *Immunol. Lett.* 88, 2, 127-134.
25. Bolte G., Osman A., Mothes T, et al. (1996) *Clin Chim Acta* 247, 59-70.
26. Secundo F., Guerrieri N. (2005) *J. Agric. Food Chem.* 53, 1757-1764.
27. Modern Pharmaceutics, 4th edition. Banker G S and Rhodes C T (eds) Marcel Dekker, NY, 2002.

The invention claimed is:

1. A method for preventing or decreasing gluten's deleterious effects on the gastrointestinal mucosa in a patient in need thereof, said method comprising administering to said patient a pharmaceutically effective amount of a synthetic polymer or copolymer, the synthetic polymer or copolymer comprising one or more of:
    (a) a copolymer of hydroxyethyl methacrylate (HEMA) and 4-styrene sulfonic acid or a salt thereof;
    (b) a copolymer of HEMA and sulfopropyl methacrylate or a salt thereof;
    (c) a polymer of 4-styrene sulfonic acid or a salt thereof; and/or
    (d) a polymer of sulfopropyl methacrylate or a salt thereof,
wherein said synthetic polymer or copolymer is able to bind to gluten, and/or bind to peptides derived from the degradation of gluten, in the gastrointestinal tract.

2. The method of claim 1, wherein the method decreases the degradation of gluten into toxic peptides in the patient.

3. The method of claim 1, wherein the method decreases the interaction of gluten or peptides derived from the degradation of gluten with the gastrointestinal mucosa of the patient.

4. The method of claim 1, wherein said administration is performed before and/or during a gluten-containing meal, or a meal suspected of containing gluten, of said patient.

5. The method of claim 1, wherein said administration is performed after a gluten-containing meal, or meal suspected of containing gluten of said patient.

6. The method of claim 1, wherein the synthetic polymer or copolymer is able to form hydrophobic interactions with gluten or peptides derived from the degradation of gluten.

7. The method of claim 1, wherein the synthetic polymer or copolymer is able to form hydrogen bonds.

8. The method of claim 1, wherein the synthetic polymer or copolymer is able to specifically bind to gluten or peptides derived from the degradation of gluten in the gastrointestinal tract.

9. The method of claim 1, wherein the synthetic polymer or copolymer is able to bind to gluten or peptides derived from the degradation of gluten in the intestinal tract.

10. The method of claim 1, wherein the synthetic polymer or copolymer is a copolymer of hydroxyethyl methacrylate (HEMA) and 4-styrene sulfonic acid sodium salt hydrate (SStNa).

11. The method of claim 1, wherein the synthetic polymer or copolymer is linear.

12. The method of claim 1, wherein the synthetic polymer or copolymer is star-shaped.

13. The method of claim 1, further comprising a zonulin antagonist or an HLA DQ2 inhibitor.

14. The method of claim 10, wherein the synthetic polymer or copolymer is able to:
    (a) bind gluten or a peptide derived from the degradation of gluten in said patient;
    (b) decrease the degradation of gluten into toxic peptides in said patient; and/or
    (c) decrease interaction of gluten, or peptides derived from the degradation of gluten, with the gastrointestinal mucosa of said patient.

15. The method of claim 10, wherein said administration is performed before, during and/or after a gluten-containing meal, or a meal suspected of containing gluten, of said patient.

16. The method of claim 10, wherein said synthetic copolymer is able to form hydrophobic interactions and/or hydrogen bonds with gluten or peptides derived from the degradation of gluten.

17. The method of claim 10, wherein the synthetic polymer or copolymer is able to specifically bind to gluten, or peptides derived from the degradation of gluten, in the gastrointestinal tract.

18. The method of claim 10, wherein the synthetic polymer or copolymer is linear or star-shaped.

19. The method of claim 10, wherein the synthetic polymer or copolymer is linear.

* * * * *

UNITED STATES PATENT AND TRADEMARK OFFICE
CERTIFICATE OF CORRECTION

PATENT NO. : 8,883,133 B2
APPLICATION NO. : 12/093423
DATED : November 11, 2014
INVENTOR(S) : Jean-Christophe Leroux and Mohamad Nasser Eddine It is certified that error appears in the above-identified patent and that said Letters Patent is hereby corrected as shown below:

On the title page, item (54) and in the specification, column 1, line 3, title, "their use" should read as --covalent bonds and their use--

Signed and Sealed this
Fourteenth Day of April, 2015

Michelle K. Lee
*Director of the United States Patent and Trademark Office*